United States Patent [19]

Tokuyama

[11] Patent Number: 5,728,384
[45] Date of Patent: Mar. 17, 1998

[54] ANTIULCER AGENT

[75] Inventor: Takashi Tokuyama, Kagawa-ken, Japan

[73] Assignee: Soken Co., Ltd., Kagawa-ken, Japan

[21] Appl. No.: 572,504

[22] Filed: Dec. 14, 1995

Related U.S. Application Data

[63] Continuation-in-part of Ser. No. 190,509, Feb. 2, 1994, abandoned.

[51] Int. Cl.$^6$ ................................................ A61K 35/78
[52] U.S. Cl. ...................... 424/195.1; 514/925; 514/926; 514/927
[58] Field of Search ............................ 424/195.1; 426/11, 426/18, 28, 29, 41, 49, 50–52, 592, 598, 599, 660, 425, 429–431, 436, 455, 465; 514/925, 926, 927

[56] References Cited

U.S. PATENT DOCUMENTS 4,943,433   7/1990   Rudor ................................ 424/195.1
5,118,503   6/1992   Sawai et al. ........................ 424/195.1

FOREIGN PATENT DOCUMENTS 04210645   7/1992   Japan .
05301823   11/1993  Japan .

OTHER PUBLICATIONS

JP 04210645, New Anti–Ulcers Drug, Containing Extract From Rice—For Treatment of Ulcers Caused by Ethanol or Stress. Derwent Abstract,92–304664, 1992.

Gut, 21(12) 1068–76 (1980 Dec.) Jayraj et al. (Abs. only).

Clin Sci. 72(4) 463–6 (1987) Jayraj et al. (Abs).

The Growing Rice Plant—An Anatomical Monograph. By Kiyochika Hoshikawa pp. 18, 19, 22, 23, 290 and 291, 1989.

*Primary Examiner*—John W. Rollins
*Attorney, Agent, or Firm*—Armstrong, Westerman, Hattori, McLeland & Naughton

[57] ABSTRACT

Ground germinated rice or an extract of polished rice or germinated rice are effective in preventing or treating ulcers.

4 Claims, No Drawings

ANTIULCER AGENT

This application is a continuation-in-part application Ser. No. 08/190,509 filed Feb. 2, 1994, now abandoned.

FIELD OF THE INVENTION

The present invention relates to an antiulcer agent obtained using rice or germinated rice as the raw material and having the activity for the prophylaxis and treatment of an ulcer by an oral administration or a subcutaneous administration.

BACKGROUND OF THE INVENTION

Hitherto, the uses of rice have been developed as 'sake', 'shochu' (Japanese spirits distilled from rice), sweet sake, vineger, 'koji' (malted rice), etc., in addition to the staple food and, thus, rice has been an indispensable one for a life from old. As other use of rice, a small rice-bran bag is known to have a cosmetic use. This is because rice has been considered to be the simple staple food or as a starch source only to the utmost. Thus, there is neither concept that rice is an effective component nor the consideration of utilizing the effective component of rice.

On the other hand, the recent daily life is called a stress age and the chances of receiving stress have been increased by the kaleidoscopic change of the living environment and the increase of the complexity of personal relations. Also, the chance of taking many victuals which do not exist in nature has been increased.

Thus, the number of persons suffering from a stomach ulcer, a duodenal ulcer, etc., by these factors has been increased and various antiulcer agents have been developed and utilized at present. The antiulcer agents which have been used at present are largely classified into a digestive power depressant, a gastric juice secretion depressant, a mucous membrane protective tissue reparative agent, etc., and are orally or subcutaneously administered. However, these preparations are isolated medicaments or synthesized medicaments, each medicament has each side effects, whereby the restrictions about the applicable objects and the using amount become severe, and an effective and safe antiulcer agent has not yet been developed and utilized.

Thus, since these conventional antiulcer agents can not be regularly used from the point of the safety, they can not be utilized for the prophylaxis and the recurrence prevention.

On the other hand, as preventives for ulcer, medicines for intestinal disorders and medicaments having the secretion preventing effect of gastric juice only are used and hence they are not said to be preventives for a ulcer in true meaning.

At present, side effects of medicaments to a human being become a problem and hence the development of a medicament having an antiulcer effect, which is a natural product, gives no side effects, and is sufficiently safe even when the medicament is regularly used as a preventive or a recurring preventing agent has been required.

The inventor already developed an antiulcer agent as disclosed in unexamined published Japanese Patent Application No. 4-210645 (210645/1962). However, the development of an antiulcer agent which can be prepared more inexpensively and more easily and has the antiulcer effect same as or better than that of the foregoing previous invention was still required.

SUMMARY OF THE INVENTION

The object of the present invention is, therefore, to provide a natural antiulcer agent obtained from rice, which is excellent in the antiulcer effect, is safe and inexpensive, and is utterly safe when the medicament is regularly used as a preventive or a recurring preventing agent for a ulcer.

The inventor has made the investigations on various vegetable components centering around rice which is the staple food from the view point of the harmonization of animals and plants and during the course thereof, it has been clarified that rice has many possibilities and effects which have never been anticipated until now. Thus, rice which has been used as the staple food and has the highest safety of which has been actually proved is adopted as the theme and the investigations for the general utilization of rice have been carried out.

As one of the themes, various investigations have been made on antiulcer agents obtained from rice. During the course of the investigations, it has been discovered that rice and germinated rice contain a component having a very remarkable antiulcer activity in both the cases of an oral administration and a subcutaneous administration and the present invention has been accomplished based on the discovery.

In the present invention, the component having the antiulcer effect contained in rice and germinated rice has not yet been clarified but it has been confirmed that rice and germinated rice treated as described below show the antiulcer effect.

(1) The ground product itself of germinated rice or a material containing the ground product.

(2) The extract itself of rice or germinated rice or a material containing the extract.

(3) The product itself obtained by acting an enzyme decomposition or koji (malted rice) to the hydrated product of rice or of germinated rice, or a material containing the foregoing product.

(4) The product itself obtained by extracting rice or germinated rice while acting thereto an enzyme decomposition or koji before the extraction, at the extraction, or after the extraction, or a material containing the foregoing product.

(5) The product itself obtained by alcohol-fermenting or organic acid-fermenting the extract of rice or of germinated rice or by alcohol-fermenting or organic acid-fermenting the product obtained by acting an enzyme decomposition or koji to rice or germinated rice, or a material containing the fermentation product.

DETAILED DESCRIPTION OF THE INVENTION

Then, the present invention is described in detail.

Now, "rice" being used in the present invention means any rice harvested not only in Japan but also in other countries, including unpolished rice such as nonglutinous rice, glutinous rice, etc., and polished rice regardless of the breed and the kind thereof. A detailed description concerning the characteristics of rice is provided in "The Growing Rice Plant, an Anatomical Monograph", by Kiyochika Hoshikawa, 1989, incorporated herein by reference. Particular reference is made to pages 18, 19, 22, 23, 290 and 291 for the specific features of rice considered in the present disclosure. Furthermore, not more than 92% polished rice bran formed at polishing rice can be used as "rice" in this invention and such a polished rice bran is inexpensive and economical. Also, germinated rice is used in the present invention.

In addition, since the effective component of rice or germinated rice is stable to heat and light, the raw materials described above may be subjected to a surface denaturation such as dipping, cooking, broiling (including sand broiling, netting broiling, hot blast broiling, etc.), cook broiling, lyophilization, etc.; a light denaturation such as an UV irradiation, etc.; press broiling such as pat rice, etc.; or a raw material treatment such as frying, etc. Also, the effect of the components is not changed by applying thereto the foregoing treatments.

Rice and germinated rice can be used effectively as they are but from the view point of practical use, it is preferred to use them as the ground products. For powdering rice and germinated rice by grinding them, a general method using a grinder or a rice-cleaning machine may be used.

In the case of germinating rice, rice with embryo buds is immersed in water or water is sprayed onto rice with embryo buds to germinate. The temperature at the germination is from 5° C. to 70° C. However, if rice gerimates, there are no restrictions on the temperature and the time for the germination. Also, if there is a possibility of rotting water during the germination, it is preferred to renew the water such that the water is not rotted or apply an antiseptic means.

In this invention, the term "germination" means the whole state of rice directly before germination to germinated rice. Germinated rice is used after being washed well. In this case, the washed germinated rice may be dried.

In the case of extracting rice or germinated rice or acting an enzyme decomposition or 'koji' to rice or germinated rice, when the raw material rice or germinated rice is ground into a granular form or a powder form, the surface area of the raw material is increased to improve the efficiency. The raw material may not be ground but in this case, a long time is required for the decomposition or the extraction of the rice tissue.

In the case of extracting rice or germinated rice with water, the efficiency is improved by increasing the extraction temprature but even at a low temperature, the extraction can be sufficiently carried out. However, when the extraction temperature is lower than 40° C., it is preferable that pH of the system is adjusted to an acidic state or an alkaline state or an antiseptic or an alcohol is added to the system to prevent the rice or germinated rice from being rotted.

The extraction time may be long or short if the effective component can be extracted and may be determined according to the extraction temperature. Also, the extraction may be carried out under pressure, at normal pressure, or under reduced pressure.

In the case of the water extraction of rice or germinated rice, the most troublesome problem is a gelatinization phenomenon. If rice is gelatinized, not only the extraction efficiency is reduced but also the practical extraction operation becomes very difficult. For preventing the occurrence of the gelatinization of rice, the extraction may be carried out with the addition of amylase or the system may be acidified with hydrochloric acid to cut the starch. By employing the foregoing method, the problem can be sufficiently solved and there is no problem for practical use in the case of employing the method.

Since the effective component in the extracted product may be stable to an acid or an alkali, it is effective to carry out the acid decomposition extraction or an alkali decomposition extraction. In this case, if necessary, a neutralization and desalting can be carried out.

Even in the case of extracting with an organic solvent, it is desirable to grind or powder rice or germinated rice as fine as possible at the extraction. As the organic solvent, a general organic solvent such as ethanol, acetone, n-hexane, methanol, etc., can be used but since an organic solvent which is noxious to a human being must be completely removed from the extract and hence the use of an organic solvent inoxious to a human being is preferable.

Also, an enzyme decomposition or 'koji' may be acted to rice or germinated rice. The "enzyme decomposition" in this invention means that one or more kinds of enzymes acting to rice or germinated rice, such as an amylolytic enzyme, a proteolytic enzyme, lipase, a fiber decomposition enzyme, a lignin decomposition enzyme, a pectin decomposition enzyme, etc., are acted.

Also, as the 'koji', there are no restrictions on the kind of the 'koji' moulds and the breedings and the kind of rice for producing 'koji'.

Furthermore, at carrying out the extraction described above, the foregoing enzyme decomposition or 'koji' may be acted thereto before the extraction, at the extraction, or after the extraction.

In the present invention, when an alcohol fermentation or an organic acid fermentation such as a lactic acid fermentation, an acetic acid fermentation, etc., is applied simultaneously with or after the treatment described above, the treatment becomes effective in the points as described below.

First, when the alcohol fermentation is applied, the concentration of the treated product becomes easy, whereby the effective component can be easily concentrated.

Also, the lactic acid fermentation improves the flavor of the product in the case of using the product for drinks, etc., and by applying the acetic acid fermentation, the product can be utilized for a seasoning liquid as vinegar. Thus, by applying the organic acid fermentation, the product can be widely used.

The product of the present invention obtained as described above is used as it is without separating residues or used after compressing and/or filtrating. When the product is used as it is, the product is subjected to a sterilization or a removal of fungi. In addition, the product may be dried and used as granules, tabulets, etc. Furthermore, the product can be used by being compounded with various foods.

Specific preferred embodiments of the invention include the following:

One method for producing a pharmaceutical composition for the treatment of gastric ulcers includes the steps of:

removing pericarp and seed coat of brown rice, removing the outside part including the aleurone layer, embryo and a part of starch storing cells until the yielding percentage of rice after polishing reaches 92 to 50%, collecting said removed outside part including the aleurone layer, embryo and the starch storing cells, adding proteolytic enzyme, lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, and squeezing the mixture by squeezer to provide a liquid product. The liquid product can be added to a pharmaceutically acceptable carrier to produce the pharmaceutical composition.

In another embodiment, a pharmaceutical composition for the treatment of gastric ulcer is produced by:

removing pericarp and seed coat of brown rice, removing the outside part including the aleurone layer, embryo and a part of starch storing cells until the yielding percentage of rice after polishing reaches 92 to 50%, collecting said removed outside part including the aleurone layer, embryo and the starch storing cells, adding proteolytic enzyme, lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, raising the temperature of the mixture gradually, extracting under boiling for 5 minutes, cooling the extract, and squeezing the mixture by squeezer to provide a liquid product. The liquid product is added to a pharmaceutically acceptable carrier to produce the pharmaceutical composition.

In yet another embodiment, the method of producing a pharmaceutical composition for the treatment of gastric ulcer contains the steps of:

removing pericarp and seed coat of brown rice, removing the outside part including the aleurone layer, embryo and a part of starch storing cells until the yielding percentage of rice after polishing reaches 92 to 50%, collecting said removed outside part including the aleurone layer, embryo and the starch storing cells, adding proteolytic enzyme lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, raising the temperature of the mixture gradually, extracting under boiling for 5 minutes, cooling the extract, adding yeast to said extract, carrying out an alcohol fermentation, squeezing the fermentation product by a squeezer to provide a liquid product; and adding the liquid product to a pharmaceutically acceptable carrier.

A pharmaceutical composition for the treatment of gastric ulcer can also be produced by the method of:

removing pericarp and seed coat of brown rice, removing the outside part including the aleurone layer, embryo and a part of starch storing cells until the yielding percentage of rice after polishing reaches 92 to 50%, collecting said removed outside part including the aleurone layer, embryo and the starch storing cells, adding proteolytic enzyme, lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, raising the temperature of the mixture gradually, extracting under boiling for 5 minutes, cooling the extract, sterilizing the extract by boiling, cooling the extract to 37° C., adding a starter previously prepared by culturing a lactic acid bacteria to the extract followed by stirring well, sealing the mixture tightly, carrying out lactic acid fermentation at 37° C. for 2 days, squeezing the fermentation product by a squeezer to provide a liquid product; and adding the liquid product to a pharmaceutically acceptable carrier.

Then, the antiulcer effect of the products of the present invention is described below.

Prophylaxis effect to the occurrence of stress ulcer:

For determining the effect as an antiulcer agent of the product of the present invention, the effect of the present invention to a restrained water-immersed stress ulcer in the oral administration was investigated. The method was carried out according to the Watanabe et al method.

That is, after fasting ddY series male mice aged 8 weeks for 24 hours, the product obtained in each of the examples described hereinafter was orally administered to the mice at 0.3 ml/mouse, after 30 minutes since then, the mice were placed in a stress gauge, and the mice were immersed in water of 15° C. up to the xiphisternum of each mouse, thereby a restrained water-immersed stress was applied to the mice. After 5 hours, each mouse was slaughtered by (luxating) the cervical vertebrae thereof and the stomach was extracted. Thereafter, 1.5 ml of a 1% formalin solution was infused into the stomach followed by immersing the stomach in the solution, whereby the stomach tissue was lightly fixed, and the stomach was allowed to stand as it was for 24 hours. Thereafter, the stomach was incised along the curvatura ventriculi major, the length (mm) of each injury formed at the glandular stomach was measured, and the sum total thereof per one mouse was shown as the ulcer coefficient.

Also, as the control, the mice orally administered with the same amount of an isotonic sodium chloride solution 30 minutes before being placed in the stress gauge were used.

For each test, 15 mice were used. The results obtained are shown in Table 1 below.

TABLE 1

| Product Obtained in Example | Doses | No. of Test Mice | Average Ulcer Coefficient |
| --- | --- | --- | --- |
| Example 1 | 0.3 ml | 15 | 10.4 |
| Example 2 | 0.3 ml | 15 | 6.3 |
| Example 4 | 0.3 ml | 15 | 2.2 |
| Example 4* | 0.3 ml | 15 | 2.1 |
| Example 5 | 0.3 ml | 15 | 0.9 |
| Example 6 | 0.3 ml | 15 | 3.1 |
| Example 8 | 0.3 ml | 15 | 2.7 |
| Example 10 | 0.3 ml | 15 | 7.1 |
| Example 12 | 0.3 ml | 15 | 5.1 |
| Example 14 | 0.3 ml | 15 | 5.4 |
| Example 16 | 0.3 ml | 15 | 4.7 |
| Example 18 | 0.3 ml | 15 | 3.8 |
| Example 20 | 0.3 ml | 15 | 5.6 |
| Example 22 | 0.3 ml | 15 | 2.8 |
| Example 24 | 0.3 ml | 15 | 1.0 |
| Example 26 | 0.3 ml | 15 | 1.6 |
| Example 28 | 0.3 ml | 15 | 1.4 |
| Example 30 | 0.3 ml | 15 | 0.2 |
| Example 32 | 0.3 ml | 15 | 0.4 |
| Example 34 | 0.3 ml | 15 | 0.7 |
| Control** | 0.3 ml | 15 | 25.2 |

(*): Product obtained as in Example 4 using glutinous rice.
(**): Isotonic sodium chloride solution was used.

As shown in Table 1, it can be seen that while the average ulcer coefficient in the mice administered with an isotonic sodium chloride solution as a control is 25.2, the average ulcer coefficient in the mice administered with the products of the present invention is very low in all the cases, which clearly shows that the oral administration of the product of the present invention is effective as an antiulcer agent to a restrained water-immersion stress ulcer.

As the result, it has been confirmed that the product of the present invention directly acts from the mucous membrane of the stomach and intestines to show an effective activity as an antiulcer agent.

In addition, when the prophylaxis effect by the rice bran extract obtained by processing a rice bran formed at rice cleaning as in Example 4 was also tested as described above, not only the extract showed no effect but also there was rather tendency of increasing the ulcer coefficient.

Then, the effect of the products of this invention to a restrained water-immersion stress ulcer by a subcutaneous administration was investigated. The method was carried out according to the Watanabe et al method as in the case of the oral administration described above.

That is, after allowing to stand for 30 minutes 15 mice (control) subcutaneously administered with 0.3 ml of an isotonic sodium solution and each of 15 mice subcutaneously administered with the product of the present invention obtained in each of the examples, the mice were placed in a stress gauge, a restrained water-immersion stress was applied to the mice, and the effectiveness to the restrained water-immersion stress ulcer by the subcutaneous administration of the products of the present invention was determined. The results are shown in Table 2 below.

TABLE 2

| Product Obtained in Example | Doses | No. of Test Mice | Average Ulcer Coefficient |
| --- | --- | --- | --- |
| Example 2 | 0.3 ml | 15 | 8.7 |
| Example 4 | 0.3 ml | 15 | 2.1 |
| Example 4* | 0.3 ml | 15 | 2.4 |
| Example 5 | 0.3 ml | 15 | 1.1 |
| Example 6 | 0.3 ml | 15 | 3.4 |
| Example 8 | 0.3 ml | 15 | 3.0 |
| Example 10 | 0.3 ml | 15 | 7.5 |
| Example 12 | 0.3 ml | 15 | 5.6 |
| Example 14 | 0.3 ml | 15 | 5.4 |
| Example 16 | 0.3 ml | 15 | 5.7 |
| Example 18 | 0.3 ml | 15 | 4.8 |
| Example 20 | 0.3 ml | 15 | 5.4 |
| Example 22 | 0.3 ml | 15 | 3.1 |
| Example 24 | 0.3 ml | 15 | 12 |
| Example 26 | 0.3 ml | 15 | 18 |
| Example 28 | 0.3 ml | 15 | 15 |
| Example 30 | 0.3 ml | 15 | 0.3 |
| Example 32 | 0.3 ml | 15 | 0.5 |
| Example 34 | 0.3 ml | 15 | 0.7 |
| Control** | 0.3 ml | 15 | 26.1 |

(*), (**): Same as in Table 1 described above.

As shown in Table 2, it can be seen that while the average ulcer coefficient in the mice subcutaneously administered with 0.3 ml of an isotonic sodium chloride solution was 26.1, the average ulcer coefficient of the mice subcutaneously administered with 0.3 ml of each product of the present invention is very low in all cases, which shows that the subcutaneous administration of the product of this invention is effective as an antiulcer agent.

The foregoing fact that the product of the present invention showed an effective antiulcer activity as an antiulcer agent by the subcutaneous administration as described above proves that not only the product of the present invention has the direct effect to a mucous membrane but also there exists in the product an effective component having an effect of fundamentally preventing the occurrence of a stomach ulcer through blood.

From the results described above, it has been confirmed that the product of the present invention is effective to the prophylaxis of the occurrence of a stress ulcer based on the component which is effective in the oral administration and the subcutaneous administration.

Then, the treatment effect of the products of the present invention to the stomach ulcer of mice was investigated.

Hitherto, for the determination of the treatment effect of a ulcer using rats, the treatment effect has been determined by the effects to (1) a 'shochu' gastrin ulcer and (2) an acetic acid ulcer. On the other hand, in the present invention a method capable of easily determining the ulcer treating effect using mouse has been established and for determining the treatment effect to the stomach ulcer of mouse, the established was used.

That is, after fasting ddY series male mice for 24 hours, the mice were placed in a stress gauge and immersed in water of 15° C. up to the xiphisternum of each mouse to apply a restrained water-immersed stress. After 5 hours since then, 0.3 ml of the product of the present invention was immediately orally administered to each mouse, after 2 hours, each mouse was slaughtered by luxating the cervical vertebrae, and the stomach was extracted. Thereafter, 1.5 ml of a 1% formalin solution was infused into the stomach, the stomach was further immersed in the solution, whereby the stomach was lightly fixed, and thereafter, the ulcer coefficient was measured.

Also, as a control, the mice orally administered with an isotonic sodium chloride solution were used.

In the test, 15 mice were used in each case.

The results obtained are shown in Table 3 below.

TABLE 3

| Product Obtained in Example | Doses | No. of Test Mice | Average Ulcer Coefficient |
| --- | --- | --- | --- |
| Example 1 | 0.3 g | 15 | 11.5 |
| Example 2 | 0.3 ml | 15 | 14.8 |
| Example 4 | 0.3 ml | 15 | 2.4 |
| Example 4* | 0.3 ml | 15 | 2.1 |
| Example 5 | 0.3 ml | 15 | 4.5 |
| Example 6 | 0.3 ml | 15 | 3.8 |
| Example 8 | 0.3 ml | 15 | 3.2 |
| Example 10 | 0.3 ml | 15 | 7.7 |
| Example 12 | 0.3 ml | 15 | 5.7 |
| Example 14 | 0.3 ml | 15 | 5.4 |
| Example 16 | 0.3 ml | 15 | 6.3 |
| Example 18 | 0.3 ml | 15 | 5.2 |
| Example 20 | 0.3 ml | 15 | 5.9 |
| Example 22 | 0.3 ml | 15 | 4.2 |
| Example 24 | 0.3 ml | 15 | 1.5 |
| Example 26 | 0.3 ml | 15 | 2.2 |
| Example 28 | 0.3 ml | 15 | 2.0 |
| Example 30 | 0.3 ml | 15 | 0.9 |
| Example 32 | 0.3 ml | 15 | 1.2 |
| Example 34 | 0.3 ml | 15 | 1.3 |
| Control** | 0.3 ml | 15 | 27.2 |

(*), (**): Same as in Table 1.

From the results shown in the above table, it can be seen that while the average ulcer coefficient in the case of orally administering an isotonic sodium chloride solution, the treatment effect to the stomach ulcer is clearly effective in all the cases of orally administering the products of the present invention.

Then, the present invention is described more practically by the following examples.

EXAMPLE 1

By immersing 1 kg of rice with germs in water of 25° C. for 3 days, the rice was germinated. After washing well the germinated rice, the germinated rice was dried at 50° C. for 24 hours and finely ground to provide 990 g of the product of the present invention.

EXAMPLE 2

Polished rice was ground by a grinder to provide 500 g of the ground product of polished rice. To the ground product was added 1,500 ml of water and after lowering pH thereof with hydrochloric acid, the mixture was allowed to stand for 10 days. Thereafter, the mixture was squeezed by a squeezer and the clear liquid obtained was neutralized to provide 1,200 ml of the product of the present invention and 760 g of residues.

EXAMPLE 3

By following the same procedure as Example 2 using 500 g of the product of this invention obtained in Example 1, 1,190 ml of other product of the present invention was obtained.

EXAMPLE 4

Polished rice was ground by a grinder to provide 500 g of the ground product of polished rice. To the ground product were added 10 g of a liquefied enzyme and 1,500 ml of water. Thereafter, the temperature of the mixture was gradually raised and after extracting under boiling for 5 minutes, the extract was cooled. Then, the extract was squeezed by a squeezer to provide 1,420 ml of the product of the present invention and 560 g of residues.

EXAMPLE 5

By following the same procedure as Example 4 using 500 g of the product of this invention obtained in Example 1, 1,400 ml of other product of the present invention was obtained.

EXAMPLE 6

Polished rice was ground by a grinder to provide 500 g of the ground product of polished rice. To the ground product was added 1,500 ml of an aqueous 2N sodium hydroxide solution and the resultant mixture was allowed to stand for 5 days. Thereafter, the mixture was squeezed by a squeezer to provide 1,350 ml of a clear liquid and 650 g of residues. By neutralizing the clear liquid with 10N hydrochloric acid, 1,480 ml of the product of the present invention was obtained.

EXAMPLE 7

By following the same procedure as Example 6 using 500 g of the product of this invention obtained in Example 1, 1,490 ml of other product of the present invention was obtained.

EXAMPLE 8

Polished rice was ground by a grinder to provide 500 g of the ground product of polished rice. To the ground product was added 1,500 ml of 95% ethanol and the mixture was allowed to stand for 5 days. Thereafter, the mixture was squeezed by a squeezer to provide 1,300 ml of a clear liquid and 650 g of residues. To the clear liquid was added 2,000 ml of water and the mixed liquid was concentrated by a rotary evaporator to provide 1,500 ml of the product of the present invention.

EXAMPLE 9

By following the same procedure as Example 8 using 500 g of the product of this invention obtained in Example 1, 1,500 ml of other product of the present invention was obtained.

EXAMPLE 10

Polished rice was ground by a grinder to provide 500 g of the ground product of polished rice. To the ground product were added 300 g of 'koji' and 1,500 ml of water and the mixture was allowed to stand for 20 hours at 55° C. Thereafter, the mixture was squeezed by a squeezer to provide 1,230 ml of the product of the present invention and 1,000 g of residues.

EXAMPLE 11

By following the same procedure as Example 10 using 500 g of the product of this invention obtained in Example 1, 1,230 ml of other product of the present invention was obtained.

EXAMPLE 12

Polished rice was ground by a grinder to provide 500 g of the ground product of polished rice. To the ground product were added 2 g of proteolytic enzyme and 1,500 ml of water and the resultant mixture was allowed to stand at 50° C. for 2 hours. Thereafter, the mixture was squeezed by a squeezer to provide 1,310 ml of the product of the present invention and 670 g of residues.

EXAMPLE 13

By following the same procedure as Example 12 using 500 g of the product of the present invention obtained in Example 1, 1,380 ml of other product of the present invention was obtained.

EXAMPLE 14

Polished rice was ground by a grinder to provide 500 g of the ground product of polished rice. To the ground product were added 2 g of lipase and 1,500 ml of water and the resultant mixture was allowed to stand at 50° C. for 20 hours. Thereafter, the mixture was squeezed by a squeezer to provide 1,290 ml of the product of the present invention and 680 g of residues.

EXAMPLE 15

By following the same procedure as Example 14 using 500 g of the product of this invention obtained in Example 1, 1,360 ml of other product of the present invention was obtained.

EXAMPLE 16

Polished rice was ground by a grinder to provide 500 g of the ground product of polished rice. To the ground product were added 2 g of a fiber decomposition enzyme and 1,500 ml of water and the resultant mixture was allowed to stand at 50° C. for 20 hours. Thereafter, the mixture was squeezed by a squeezer to provide 1,330 ml of the product of the present invention and 650 g of residues.

EXAMPLE 17

By following the same procedure as Example 16 using 500 g of the product of this invention obtained in Example 1, 1,370 ml of other product of the present invention was obtained.

EXAMPLE 18

Polished rice was ground by a grinder to provide 500 g of the ground product of polished rice. To the ground product were added 2 g of an amylolytic enzyme and 1,500 ml of water and the resultant mixture was allowed to stand at 55° C. for 20 hours. Thereafter, the mixture was squeezed by a squeezer to provide 1,380 ml of the product of the present invention and 600 g of residues.

EXAMPLE 19

By following the same procedure as Example 18 using 500 g of the product of this invention obtained in Example 1, 1,400 ml of other product of the present invention was obtained.

EXAMPLE 20

Polished rice was ground by a grinder to provide 500 g of the ground product of polished rice. To the ground product were added 2 g of a pectin decomposition enzyme and 1,500 ml of water and the resultant mixture was allowed to stand at 50° C. for 20 hours. Thereafter, the mixture was squeezed by a squeezer to provide 1,320 ml of the product of the present invention and 660 g of residues.

EXAMPLE 21

By following the same procedure as Example 20 using 500 g of the product of this invention obtained in Example 1, 1,300 ml of other product of the present invention was obtained.

EXAMPLE 22

Polished rice was ground by a grinder to provide 500 g of the ground product of polished rice. To the ground product were added 2 g of a proteolytic enzyme, 2 g of lipase, 2 g of a fiber decomposition enzyme, 2 g of an amylolytic enzyme, 2 g of a pectin decomposition enzyme, and 1,500 ml of water and the resultant mixture was allowed to stand at 50° C. for 20 hours. Thereafter, the mixture was squeezed by a squeezer to provide 1,420 ml of the product of the present invention and 560 g of residues.

EXAMPLE 23

By following the same procedure as Example 22 using 500 g of the product of this invention obtained in Example 1, 1,440 ml of other product of the present invention was obtained.

EXAMPLE 24

By following the same procedure as Example 22, 2,000 g of the enzyme decomposition product of polished rice was obtained. Thereafter, the temperature thereof was gradually raised and after extracting under boiling for 5 minutes, the extract was cooled. Thereafter, the extract was squeezed by a squeezer to provide 1,400 ml of the product of the present invention and 550 g of residues.

EXAMPLE 25

By following the same procedure as Example 24 using 500 g of the product of this invention obtained in Example 1, 1,420 ml of other product of the present invention was obtained.

EXAMPLE 26

Polished rice was ground by a grinder to provide 500 g of the ground product of polished rice. To the ground product were added 300 g of 'koji' and 1,500 ml of 40% ethanol and the resultant mixture was allowed to stand at 55° C. for 48 hours. Thereafter, the mixture was squeezed by a squeezer to provide 1,300 ml of a clear liquid and 850 g of residues. Then, to the clear liquid was added 1,000 ml of water and the mixture was concentrated by a rotary evaporator to provide 1,300 ml of the product of the present invention.

EXAMPLE 27

By following the same procedure as Example 26 using 500 g of the product of this invention obtained in Example 1, 1,300 ml of other product of the present invention was obtained.

EXAMPLE 28

By following the same procedure as Example 4, 2,000 g of the extract of polished rice was obtained. To the extract were added 2 g of a proteolytic enzyme, 2 g of lipase, 2 g of a fiber decomposition enzyme, 2 g of an amylolytic enzyme, and 2 g of a pectin decomposition enzyme and the resultant mixture was allowed to stand at 50° C. for 24 hours. Thereafter, the mixture was squeezed by a squeezer to provide 1,400 ml of the product of the present invention and 580 g of residues.

EXAMPLE 29

By following the same procedure as Example 28 using 500 g of the product of this invention obtained in Example 1, 1,390 ml of other product of the present invention was obtained.

EXAMPLE 30

By following the same procedure as Example 24, 2,000 g of the enzyme decomposition extract of polished rice was obtained. To the enzyme decomposition extract was added yeast and an alcohol fermentation was carried out. Thereafter, the fermentation product was squeezed by a squeezer to provide 1,880 ml of the product of the present invention and 80 g of residues.

EXAMPLE 31

By following the same procedure as Example 30 using 500 g of the product of this invention obtained in Example 1, 1,800 ml of other product of the present invention was obtained.

EXAMPLE 32

By following the same procedure as Example 24, 2,000 g of the enzyme decomposition extract of polished rice was obtaned. After sterilizing the enzyme decomposition extract by boiling, the extract was cooled to 37° C., and 200 ml of a starter previously prepared by culturing a lactic acid bacteria was added thereto followed by stirring well. Thereafter, the mixture was sealed tightly and the lactic acid fermentation was carried out at 37° C. for 2 days. Then, the fermentation product was squeezed by a squeezer to provide 1,380 ml of the product of the present invention and 590 g of residues.

EXAMPLE 33

By following the same procedure as Example 32 using 500 g of the product of this invention obtained in Example 1, 1,400 ml of other product of the present invention was obtained.

EXAMPLE 34

To 1,000 ml of the product of this invention obtained in Example 24 was added 80 ml of 95% ethanol and the acetic acid fermentation was carried out for 20 hours. Thereafter, the fermentation product was filtrated to provide 990 ml of the product of the present invention.

EXAMPLE 35

By following the same procedure as Example 34 using 500 g of the product of this invention obtained in Example 1, 1,000 ml of other product of the present invention was obtained.

Then, examples of the case of preparing tables by compounding the product of the present invention and the case of preparing a soft drink using the product of the present invention are described below. In addition, the present invention is not limited to the compounding examples.

EXAMPLE 36 (Tablet)

By drying 100 g of the product obtained in Example 24 by freeze-drying, 20 g of the dried product was obtained. By using 10 g of the dried product, tablets were prepared as described below.

| Product of the Invention | 10 g |
|---|---|
| Polyethylene Glycol 6000 | 10 g |
| Sodium Laurylsulfate | 1.5 g |
| Corn Starch | 3 g |
| Milk Sugar | 25 g |
| Magnesium Stearate | 0.5 g |

After weighting each component described above, polyethylene glycol 6000 was heated to a temperature of from 70° C. to 80° C. and after mixing it with the product of this invention, sodium laurylsulfate, corn starch, and milk sugar, the mixture was cooled as it was. The solidified mixture was granulated by a grinder. Then, after mixing the granules with magnesium stearate, the mixture was tableted to form tablets each having a weight of 250 mg.

EXAMPLE 37 (Soft Drink)

In the example, the product of this invention obtained in Example 22 was used.

| Product of the Invention | 15% by weight |
|---|---|
| Licorice Extract | 0.01% by weight |
| Sugar | 4% by weight |
| Lemon Juice | 2.5% by weight |
| Purified Water | 78.49% by weight |

By mixing the above components by an ordinary manner, a soft drink was obtained.

As described above in detail, each of the products of the present invention shows a remarkable effect to a digestive ulcer. The fact that the products of the present invention show great effects in the oral administration and the subcutaneous administration shows that the products of the present invention can be practically used as internal medicines and injections and wide uses of the products are expected. It is epoch-making that the products having such a remarkable antiulcer activity are easily obtained at a low cost from rice the safety of which has been proved.

Furthermore, the products of the present invention have not only the treatment effect of a ulcer but also the prophylactic effect for a ulcer since there is no problem even when the product is regularly used. Thus, the products of the present invention give very excellent achievements in the point of a preventive medicine and give good merits to persons suffered from a ulcer from the view point of the recurrence prevention for them.

What is claimed is:

1. A pharmaceutical composition for the treatment of gastric ulcer, produced by the method of:

removing pericarp and seed coat of brown rice, removing an outside part of the rice including the aleurone layer, embryo and a part of starch storing cells until the yielding percentage of rice after polishing reaches 92 to 50%, collecting said removed outside part including the aleurone layer, embryo and the starch storing cells, adding proteolytic enzyme, lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, and squeezing the mixture by squeezer to provide a liquid product;

the pharmaceutical composition comprising said liquid product and a pharmaceutically acceptable carrier.

2. A pharmaceutical composition for the treatment of gastric ulcer produced by the method of:

removing pericarp and seed coat of brown rice, removing an outside part of the rice including the aleurone layer, embryo and a part of starch storing cells until the yielding percentage of rice after polishing reaches 92 to 50%, collecting said removed outside part including the aleurone layer, embryo and the starch storing cells, adding proteolytic enzyme, lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, raising the temperature of the mixture gradually, extracting under boiling for 5 minutes, cooling the extract, and squeezing the mixture by squeezer to provide a liquid product;

the pharmaceutical composition comprising the liquid product and a pharmaceutically acceptable carrier.

3. A pharmaceutical composition for the treatment of gastric ulcer, produced by the method of:

removing pericarp and seed coat of brown rice, removing an outside part of the rice including the aleurone layer, embryo and a part of starch storing cells until the yielding percentage of rice after polishing reaches 92 to 50%, collecting said removed outside part including the aleurone layer, embryo and the starch storing cells, adding proteolytic enzyme, lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, raising the temperature of the mixture gradually, extracting under boiling for 5 minutes, cooling the extract, adding yeast to said extract, carrying out an alcohol fermentation, and squeezing the fermentation product by a squeezer to provide a liquid product;

the pharmaceutical composition comprising the liquid product and a pharmaceutically acceptable carrier.

4. A pharmaceutical composition for the treatment of gastric ulcer, produced by the method of:

removing pericarp and seed coat of brown rice, removing an outside part of the rice including the aleurone layer, embryo and a part of starch storing cells until the yielding percentage of rice after polishing reaches 92 to 50%, collecting said removed outside part including the aleurone layer, embryo and the starch storing cells, adding proteolytic enzyme, lipase, a fiber decomposition enzyme, an amylolytic enzyme, a pectin decomposition enzyme and water to said removed outside part including the aleurone layer, embryo and the starch storing cells, maintaining the resultant mixture at 50° C. for 20 hours, raising the temperature of the mixture gradually, extracting under boiling for 5 minutes, cooling the extract, sterilizing the extract by boiling, cooling the extract to 37° C., adding a starter previously prepared by culturing a lactic acid bacteria to the extract followed by stirring well, sealing the mixture tightly, carrying out lactic acid fermentation at 37° C. for 2 days, and squeezing the fermentation product by a squeezer to provide a liquid product;

the pharmaceutical composition comprising the liquid product and a pharmaceutical acceptable carrier.

* * * * *